US007829124B2

(12) United States Patent
Ott et al.

(10) Patent No.: US 7,829,124 B2
(45) Date of Patent: Nov. 9, 2010

(54) **USE OF *PHYLLANTHUS* CONSTITUENTS FOR TREATING OR PREVENTING INFECTIONS CAUSED BY HEPATITIS B-VIRUSES**

(76) Inventors: Michael Ott, Medizinische Hochschule Hannover, Forschungszentrum Oststadt, Labor Für Zell- und Gentherapie, Pasteurallee 5, 30655 Hannover (DE); Michael P. Manns, Sonnenallee 23, 30916 Isernhagen HB (DE)

( * ) Notice: Subject to any disclaimer, the term of this patent is extended or adjusted under 35 U.S.C. 154(b) by 0 days.

(21) Appl. No.: 11/563,540

(22) Filed: Nov. 27, 2006

(65) Prior Publication Data

US 2007/0264359 A1 Nov. 15, 2007

Related U.S. Application Data

(62) Division of application No. 10/476,059, filed as application No. PCT/EP02/04641 on Apr. 26, 2002, now abandoned.

(30) Foreign Application Priority Data

Apr. 26, 2001 (DE) .................................. 101 20 627

(51) Int. Cl.
*A61K 36/00* (2006.01)
(52) U.S. Cl. ....................................... 424/725; 514/894
(58) Field of Classification Search ...................... None
See application file for complete search history.

(56) References Cited

U.S. PATENT DOCUMENTS

| 28,754 | A |  | 2/1904 | Von Keudell et al. ........ | 424/725 |
|---|---|---|---|---|---|
| 33,275 | A |  | 2/1904 | Kreuter et al. ............... | 424/725 |
| 161,477 | A |  | 8/1904 | Wagner et al. ............... | 424/725 |
| 4,388,457 | A |  | 6/1983 | Pettit ............................ | 536/4.1 |
| 4,673,575 | A |  | 6/1987 | Venkateswaran et al. . | 424/195.1 |
| 4,937,074 | A |  | 6/1990 | Venkateswaran et al. . | 424/195.1 |
| 5,529,778 | A |  | 6/1996 | Rohatgi ..................... | 424/195.1 |
| 5,571,441 | A |  | 11/1996 | Andon et al. .................... | 252/1 |
| 5,648,089 | A |  | 7/1997 | Shawkat ..................... | 424/434 |
| 5,854,233 | A |  | 12/1998 | McLean ........................ | 514/211 |
| 6,136,316 | A | * | 10/2000 | Mehrotra et al. ............. | 424/725 |
| 6,258,831 | B1 |  | 7/2001 | Camden ...................... | 514/361 |
| 6,586,015 | B1 | * | 7/2003 | Gebhardt et al. ............ | 424/725 |
| 2002/0054921 | A1 | * | 5/2002 | Von Keudell et al. ........ | 424/725 |

FOREIGN PATENT DOCUMENTS

| WO | 8909059 | 10/1989 |
|---|---|---|
| WO | 9004968 | 5/1990 |
| WO | 0061161 | 9/2000 |

OTHER PUBLICATIONS

Dusheiko, Treatment and Prevention of Chronic Viral Hepatitis, 1995, Pharmac. Ther., 65, 47-73.*

Ono-Nita et al., YMDD Motif in Hepatitis B Virus DNA Polymerase Influences on Replication and Lamivudine Resistance: A Study by In Vitro Full-Length Viral DNA Transfection, 1999, 29, 939-945.*

Thyagarajan et al., "Effect of Phyllanthus Amarus on Chronic Carriers of Hepatitis B Virus," *The Lancet*, Oct. 1, 1988, pp. 764-766.

Venkateswaran et al., "Effects of an extract from *Phyllanthus niruri* on hepatitis B and woodchuck hepatitis viruses: In vitro and in vivo studies," *Proc. Natl. Acad. Sci. USA*, vol. 84, pp. 274-278, Jan. 1987.

Thyagarajan et al., "In vitro inactivation of HBsAg by *Eclipta alba* Hassk and *Phyllanthus niruri* Linn," *Indian J Med Res* 76 (Suppl), pp. 124-130, Dec. 1982.

Syamasundar et al., "Antihepatotoxic principles of *Phyllanthus niruri* herbs,"*J Ethnopharmacol* 14(1):41-4 Sep. 1985. Abstract only from National Library of Medicine: IGM Full Record Screen.

del Barrio Alonso et al., "The in-vitro inactivation of HBsAg by extracts of plants in the genus *Phyllanthus*," *Rev Cubana Med Trop.*, 47(2):127-130, 1995. Abstract only from National Library of Medicine: IGM Full Record Screen.

Doshi et al., "A two-stage clinical trial of *Phyllanthus amarus* in hepatitis B carriers: failure to eradicate the surface antigen," *Indian J Gastroenterol.*, 13(1):7-8, 1994. Abstract only from National Library of Medicine: IGM Full Record Screen.

el-Mekkway et al., "Inhibitory effects of Egyptian folk medicines on human immunodeficiency virus (HIV) reverse transcriptase," *Chem Pharm Bull* (Tokyo), 43(4):641-8, 1995. Abstract only from National Library of Medicine: IGM Full Record Screen.

Wang et al., "Herbs of the genus *Phyllanthus* in the treatment of chronic hepatitis B: observations with three preparations from different geographic sites," *J Lab Clin Med.*, 126(4):350-2, Oct. 1995. Abstract from National Library of Medicine: IGM Full Record Screen.

Wang et al., "Efficacy of *Phyllanthus* spp. in treating patients with chronic hepatitis B," *Chung Kuo Chung Yao Tsa Chih.*, 19(12):750-1, 764, 1994. Abstract only from National Library of Medicine: IGM Full Record Screen.

Powis et al., "High-performance liquid chromatographic assay for the antitumor glycoside phyllanthoside and its stability in plasma of several species," *J Chromatogr*, 342(1):129-34, Jul. 12, 1985. Abstract only from National Library of Medicine: IGM Full Record Screen.

(Continued)

*Primary Examiner*—Michele Flood
*Assistant Examiner*—Catheryne Chen
(74) *Attorney, Agent, or Firm*—Baker Botts L.L.P.

(57) ABSTRACT

The disclosure relates to a method of inhibiting synthesis of viral DNA in a mammal infected with a hepatitis B virus. This method includes administering at least one *Phyllanthus* component or substance to a mammal infected with the hepatitis B virus. It also includes inhibiting hepatitis B viral DNA synthesis in the mammal using the *Phyllanthus* component or substance. The disclosure also relates to a method of inhibiting viral gene expression in a mammal infected with a hepatitis B virus. This method includes administering at least one *Phyllanthus* component or substance to a mammal infected with the hepatitis B virus. It also includes inhibiting expression of at least one hepatitis B viral gene in the mammal using the *Phyllanthus* component or substance. These methods may form part of a method of preventing or treating hepatitis B infection.

17 Claims, 1 Drawing Sheet

OTHER PUBLICATIONS

Zhou Shiwen Xu Chuanfu et al., "Mechanism of protective action of *Phyllanthus urinaria* L. against injuries of liver cells," *Zhongguo Zhongyao Zazhi*, 22(2):109-111,129; 1997. Abstract only from Datenbank BIOSIS bei STN:AN 1997:211857 BIOSIS, DN PREV 199799511060.

Asha et al., "Preliminary evaluation of the antihepatotoxic activity of *Phyllanthus kozhikodianus, P. maderaspatensis* and *Solanum indicum*," *Fitoterapia*, 69(3):255-259, 1998. Abstract only from Database Biosis 'Online! Biosciences Information Service, Philadelphia, PA, US; 1998.

Jeena et al., "Effect of *Emblica officinalis, Phyllanthus amarus* and *Picrorrhiza kurroa* on N-nitrosodiethylamine induced hepatocarcinogenesis," *Cancer Letters*, 136(1):11-16, 1999. Abstract only from Database Biosis 'Online! Biosciences Information Service, Philadelphia, PA, US; Feb. 8, 1999.

Hu et al., "Process for preparing Gynostemma pentaphylla throat-moistening tablets—useful for treating bronchitis, asthma, and cancer." Abstract only from Chemical Patents Index, Documentation Abstracts Journal Derwent Publications, London: 19.3.99,Nr.99-081999/08 zu: CN 1194857-A, Oct. 15, 2005.

S. Jayaram et a., Indian J. Virol. Vo. 13, No. 1, pp. 59-64 Efficacy of *Phyllanthus amarus* Treatment in Acute Viral Hepatitis A,B and Non A Non B: An Open Clinical Trail (Jan. 1997).

P. Ferenci Gut 1993; supplement: S69-S73 Historical Treatment of Chronic Hepatitis B and Chronic Hepatitis C.

Steven P. Lawrence, M.D., Advances in Internal Medicine, vol. 45 2000 Mosby, Inc., Advances in the treatment of hepatitis C, Oct. 15, 2005.

Nippon Mektron KK (assignee), "Lipid metabolism improving and liver disturbance inhibitory agents—comprise organic solvent or water extract of Euphorbiaceae family, *Phyllanthus niruri*." Abstract only from Chemical Patents Index, Documentation Abstracts Journal Derwent Publications, London: 19.12.97,Nr.97-508797/47 zu: JP 09241176 A, Oct. 15, 2005.

Hou et al., "SOD prepared from *Phyllanthus emblica* used as health food additive." Abstract only from Chemical Patents Index, Documentation Abstracts Journal Derwent Publications, London: 12.12.97,Nr.97-490386/46 zu: CN 1121783 A, Oct. 15, 2005.

Mikimoto Seiyaku KK (assignee), "Cosmetic material having good skin-moisturising effect—consists of compounded mixt. of cholesteric liq. crystal and one or more of e.g. *Piper longum, P. chaba* etc." Abstract only from Chemical Patents Index, Documentation Abstracts Journal Derwent Publications, London: 29.9.95,Nr.95-252224/33 zu: JP 07157420 A, Oct. 15, 2005.

Mikimoto Seiyaku KK (assignee), "Antioxidants used in lotions, creams and emulsions—contain solvent extract from e.g. *Nigella savia, Munronia pumila* or *Borrelia hispida*." Abstract only from Chemical Patents Index, Documentation Abstracts Journal Derwent Publications, London: 8.9.95,Nr.95-228590/30 zu: JP 07138126 A, Oct. 15, 2005.

Cao et al., "Antioxidant for cosmetic products." Abstract only from Chemical Patents Index, Documentation Abstracts Journal Derwent Publications, London: 8.9.95,Nr.95-224715/30 zu: CN 1086532 A, Oct. 15, 2005.

Xiao et al., "Extraction of *Phyllanthus emblica* polysaccharides (PePS) and its scavenging effect on oxygen radical," *Zhongguo Yaoxue Zazhi* (Beijing), 33(5):279-281, 1998. Abstract from Chemical Abstracts 130:452b.

Joy et al., "Inhibition of *Phyllanthus amarus* of hepatocarcinogenesis induced by N-nitrosodiethylamine," *Journal of Clinical Biochemistry and Nutrition*, 24(3):133-139, 1998. Abstract only from Datenbank BIOSIS bei STN:AN 1999:13953 BIOSIS, DN PREV 199900013953.

Potturi et al., "Protective effect of *Phyllanthus fraternus* against thioacetamide-induced mitochondrial dysfunction," *Journal of Clinical Biochemistry and Nutrition*, 22(2):113-123, 1997. Abstract only from Datenbank BIOSIS bei STN:AN 1997:4431146 BIOSIS, DN PREV 199799742349.

Ihantola-Vormisto et al., Plant Medica (Dec. 1997), 63(6): 518-524. Anti-inflammatory activity of extracts from leaves of *Phyllanthus emblica*.

Xia Quan et al., "Ethnopharmacology of *Phyllanthus emblica* L.," *Zhongguo Zhongyao Zazhi*, 22(9):515-518, 525, 574; 1997. Abstract only from Database Biosis 'Online! Biosciences Information Service, Philadelphia, PA, US.

Database BIOSIS Online! Bioscience Information Service, Philadelphia, PA, US; 1999 Houghton P. J. et al., "The anti-HIV activity of an aqueous extract and polyphenolic compounds of *Phyllanthus amarus*", Database accession No. PREV199900538759 XP-002191772, abstract & Journal of Pharmacy and Pharmacology, vol. 51, No. Suppl., 1999, p. 100 136th British Pharmaceutical Conference; Cardiff, Wales, UK; Sep. 13-16, 1999 ISSN: 0022-3573.

Suresh et al., "Augmentation of murine natural killer cell and antibody dependent cellular cytotoxicity activities by *Phyllanthus emblica*, a new immunomodulator," *J Ethnopharmacol*, 44(1):55-60, Aug. 1994, Abstract only from Database Biosis 'Online! Biosciences Information Service, Philadelphia, PA, US.

Calixto et al., "Antispasmodic effects of an alkaloid extracted from *Phyllanthus sellowianus*: a comparative study with papaverine," *Braz J Med Biol Res*, 17(3-4):313-21, 1984. Abstract only from National Library of Medicine: IGM Full Record Screen.

Shanmugasundaram et al., "Anna Pavala Sindhooram—an antiatherosclerotic Indian drug," *J Ethnopharmacol*, 7(3):247-65, May 1983. Abstract only from National Library of Medicine: IGM Full Record Screen.

Unander et al., "Uses and bioassays in *Phyllanthus* (Euphorbiaceae): a compilation II. The subgenus *Phyllanthus*," *Journal of Ethnopharmacology*, 34: 97-133, 1991.

Lee et al., "Regulation of Hepatitis B Virus Replication and Gene Expression by an Extract from *Phyllanthus niruri*," AASLD Abstracts p. 117A, (#241) *Hepatology*, vol. 18, No. 4, Pt. 2, 1993.

Chintalwar et al., "An immunologically active arabinogalactan from *Tinospora cordifolia*," *Phytochemistry* 52:1089-1093, 1999.

Matthée et al., "HIV Reverse Transcriptase Inhibitors of Natural Origin," *Planta Medica* 65:493-506, 1999.

*Neueste Literatur zu Polysacchariden mit Immunstimulierender Wirkung*, Chapters in Immunomodulatory Agents from Plants, by H. Wagner (editor), Birkhäuser Verlag Basel-Boston-Berlin, 1999, pp. 1-39, 89-104; 161-201; 203-221; 325-356.

Thabrew et al., J of Ethnopharmacology (1991), 33(1-2): 63-66. Immunomodulatory activity of three Sri-Lankan medicinal plants used in hepatic disorders.

Paya et al., Phytotherapy Research (1996), 10: 228-232. Inhibitory effects of various extracts of Argentine plant species on free-radical-mediated reactions and human neutrophil functions.

Hagers Handbuch der Pharmazeutischen Praxis, 5. Ed., Folgeband 3, Drogen L-Z, Springer Verlag, Heidelberg 1998, pp. 338-352.

Ihantola-Vormisto et al., Plant Medica (Dec. 1997), 63(6): 518-524, Anti-inflammatory activity of extracts from leaves of *Phyllanthus emblica*.

Database BIOSIS Online! Bioscience Information Service, Philadelphia, PA, US; 1992 Hayamizu K. et al., "Retroviral reverse transcriptase-inhibitory activity of flavonoid and tannin compounds", Database accession No. PREV199294037003 XP-00219773, abstract only & Bulletin of The College of Agriculture & Veterinary Medicine Nihon, No. 49, 1992, pp. 35-41, 1992 ISSN: 0078-0839.

\* cited by examiner

Figure 1 (a)

Wild type

Figure 1 (b)

Mutant

USE OF *PHYLLANTHUS* CONSTITUENTS FOR TREATING OR PREVENTING INFECTIONS CAUSED BY HEPATITIS B-VIRUSES

This application is a divisional application under 35 U.S.C. §121 of U.S. patent application Ser. No. 10/476,059, filed May 26, 2004 now abandoned, which is a National Stage of International Application No. PCT/EP02/04641, filed Apr. 26, 2002, which claims priority to German Patent Application No. 10120627.5, filed Apr. 26, 2001.

The invention relates to the use of one or more *Phyllanthus* component(s) or substances or mixtures of substances obtained therefrom for the prevention or treatment of infectious diseases caused by a hepatitis B virus which is resistant to nucleoside analogues or in the development or progression of which a hepatitis B virus resistant to nucleoside analogues plays a role. Furthermore, the invention relates to the use of one or more *Phyllanthus* component(s) or substances or mixture of substances obtained therefrom for the production of a pharmaceutical composition for the prevention or treatment of infectious diseases caused by a hepatitis B virus which is resistant to nucleoside analogues or in the development or progression of which a hepatitis B virus resistant to nucleoside analogues plays a role. Furthermore, the invention relates to the use of one or more *Phyllanthus* component(s) or substances or mixtures of substances obtained therefrom for the inhibition of the growth of a hepatitis B virus which is resistant to nucleoside analogues. Moreover, the invention relates to methods for the prevention or treatment of infectious diseases in a mammal caused by a hepatitis B virus which is resistant to nucleoside analogues or in the development or progression of which a hepatitis B virus resistant to nucleoside analogues plays a role, wherein one or more *Phyllanthus* component(s) or substances or mixtures of substances obtained therefrom are administered to the mammal. Furthermore, the invention relates to methods for the inhibition of the growth of a hepatitis B virus resistant to nucleoside analogues, wherein one or more *Phyllanthus* component(s) or substances or mixtures of substances obtained therefrom are contacted with the viruses. In a preferred embodiment of the invention, the nucleoside analogues are selected from the group consisting of Lamivudine and Famciclovir.

The plant genus *Phyllanthus* belongs to the subfamily of the Phyllanthoideae which belongs to the family of the Euphorbiaceae. The genus *Phyllanthus* comprises about 700 species in total which have their origin in the tropical and subtropical areas in Australia, China, the Philippines, Thailand, Indonesia, Burma, India, East and West Africa as well as North America, Mexico, Cuba, the Caribbean and Venezuela. Representatives of the genus *Phyllanthus* are found in the Northern temperate zones very rarely only.

Due to the heterogeneity of the genus *Phyllanthus*, only few genus-specific features are known. The majority of the representatives of the genus *Phyllanthus* are monoecious or dioecious herbs, bushes or trees with varied growth (habitus) exhibiting stalks or branches differentiated into two to three different types. Thus, *Phyllanthus* has both straight long shoots of unlimited growth and short shoots and horizontal leafy or blossomy short shoots of limited growth. Often, two different types of leaves: are observed, wherein the non-foliage leaves are found on the upward and short shoots and the foliage leaves are found on the horizontal shoots. In general, the blossoms are small and axillar, whereby the female blossoms including their flower stalks and sepals are more robust than the male blossoms. Since there are no clear generic boundaries between the different genuses, and some *Phyllanthus* species can be categorised into various genuses according to point of view, it is very difficult to get a clear picture of sufficient genus-specific ingredients and groups of ingredients. The only uniform point is the lack of latex which is considered a family feature of the subfamily Phyllanthoideae. Some characteristic groups of substances, however, are more or less widespread in *Phyllanthus*. In this context, alkaloids, in particular the alkaloids of the prevalent securinine type, are to mention, which only occur in some species. Alkaloids were detected, for example, in all the parts of the plants of *Phyllanthus niruri*. Furthermore, compounds belonging to the cyanogenic glycosides occur occasionally. They belong to the tyrosine-derived descendants of the class. A typical representative thereof is taxiphyllin and 2-hydroxy-2-(4-hydroxyphenyl)acetonitrile in the leaves of *Phyllanthus gasstroemii*. Tanning agents, in particular tannins and ellagitannins as well as their precursors preferably occur on wooden species in the tropics. In this context, the main representatives are *Phyllanthus emblica* with Phyllemblin (ethyl gallat) in the fruit. Furthermore, Phyllanthusine, an ellagitannin derivative in the herb of *Phyllanthus amarus*, is described. A further big group of ingredients relates to lignanes, while in the herb of *Phyllanthus amarus* and in all the parts of *Phyllanthus niruri*, lignanes such as, for example, Phyllanthin and cycloliganes or tetraliganes such as, for example, Hypophyllanthin occur. Moreover, sesquiterpenes in *Phyllanthus acuminatus* are described which chemically belong to the epoxides of tricyclic sesquiterpenes with spiran structure and partly ester-like-bound bioses. In comparison, triterpenes often occur in all parts of plants. Apart from Phytosterol (sitosterol), descendants of the Friedelan, Olean and Lupan type (betulin and glochidonol in *Phyllanthus reticulatus*), the occurrence of a compound of the Euphane type is noticeable, such as e.g. Phyllanthenol in *Phyllanthus niruri*.

Particularly *Phyllanthus amarus* and *Phyllanthus niruri* are used in folk medicine e.g. in Nigeria, Cuba or Jamaica in the case of fever (Unander et al. 1991 J. Ethno. Pharmacol. 34:97-133). Apart from that, the herb of some *Phyllanthus* species is used for diarrhea, for increasing the amount of urine, as a laxative and for spasms and colics. Moreover, the effectiveness of *Phyllanthus* in diabetes in described (Unander ibid), whereas the effectiveness of these applications, however, is not proven scientifically.

In scientific studies it could be shown that a series of hydrolysable tanning agents of the genus *Phyllanthus* inhibits important eukaryotic protein kinases such as the cAMP-dependent protein kinase of the rat liver, the $CA^{2+}$-dependent protein kinase of the wheat embryo, the $CA^{2+}$- and phopholipid-dependent protein kinase C (PKC) of the rat brain, whereas the tanning agents amariin, geraniin and the phenazine-derivative of the geraniin each are most effective. Moreover, there is scientific evidence for an antimicrobial effect of a dry extract of *Phyllanthus amarus*, which was extracted from the plant with 95% ethanol backflow for three hours and inhibited the growth of *Bacillus subtilis* and *Staphylococcus aureus*. In this context, in an agar plate diffusion test, when 0.1 ml of this aqueous extract was administered at a concentration of 50 mg/ml, a moderate inhibitory effect (inhibition zone <15 mm) took place; a positive control of 0.1 ml streptomycin at a concentration of 10 mg/ml caused an inhibition zone of 35 mm. In the same test system, the extract against *Pseudomonas aeruginosa, Escherichia coli, Aspergillus niger* and *Candida albicans* was ineffective. In contrast, a dry extract of the whole plant which was extracted with methanol at 20° C. showed an effect against *Staphylococcus aureus*, but not against *E. coli, A. niger* and *C. albicans*.

Amongst the human pathogenic viruses with a double-stranded DNA genome, five different virus families, in particular, are to be mentioned: Hepadnaviridae, Papovaviridae, Adenoviridae, Herpesviridae and Poxviridae. In nearly all the families (exception Poxviridae), there are representatives which can cause persistent infections in humans. In this context, herpes-, papova- and hepadnaviruses are closely related to tumor diseases in humans, which leads to the conclusion that double-stranded DNA viruses is capable of influencing the regulation of cell division and of cell death.

From a developmental point of view, the family Hepadnaviridae the prototype of which is the hepatitis B virus (HBV) is close to the Retroviridae. Many details of its replication cycle let assume that, in the course of the evolution, both families have developed from a common precursor. The most essential common feature is the fact that both virus families have reverse transcriptases (RT) which are crucial for the replication of both virus families. At the same time, this suggests that this essential component of the virus is also an important target for therapeutics.

Transfer of HBV takes place by blood or body fluids, whereby the human serves as virus reservoir; however, an experimental transfer to chimpanzees is possible. The concentration of infectious particles in acutely or chronically infected patients can reach a level of $10^9$/ml blood. The virus can be passed on to the child by the infected pregnant mother rarely before, but mostly during birth. This is the case mainly in the highly endemic areas of East Asia, Central and West Africa, where about 20-80% of the population is infected with HBV. At the moment, it is assumed that about 350 million people are chronically infected with HBV. In Germany, endemic virus spreading is only sporadic; only about 0.5% of the population are HbsAg-positive and about 5% have antibodies.

The target organ of HBV is the liver. Upon infection, after an incubation period of about 2-6 months, acute hepatitis may occur. In 65% of the cases, the infection shows no symptoms, whereas in 35% of the cases, the patients develop an inflammation of the liver. Thus, the main symptom of an acute hepatitis is the development of a jaundice (icterus) and an enlargement of the liver at the same time. In addition, aplastic anaemia and exanthems. Mostly, healing of the hepatitis is achieved after 4 to 6 weeks. However, even after an improvement of the acute condition, the inflammation of the liver can turn into a chronic state. About 5-10% of all HBV infections in adults take this chronic course. If the infection takes place pre- or perinatally, however, up to 90% take a chronic course, which, particularly in the endemic regions represents a massive problem. 60% of the chronically infected patients remain asymptomatic carriers of the virus. The symptomatic, chronic infections are divided into two forms. One differentiates between chronically aggressive progressive hepatitis (CAH) and chronically persistent hepatitis (CPH), whereby CPH can turn into CAH. Consequences of a chronic disease are liver cirrhosis and hepatocellular carcinoma (HCC).

Each year, about 250 000 people die of the consequences of this tumor. HCC is more likely to occur in people with a chronically persisting HBV infection, whereas the likelihood to get an HCC increases with prolonged infection. One reason for the development of HCC is the integration of the viral DNA into the host genome. In this context, the opening of the circular DNA takes place in the region of the origin replication so that no virus, but the HBs- and X-gene still can be expressed, wherein the X-protein, in particular, is suspected to have transforming characteristics. Furthermore, the unspecific integration of the genome itself can lead to cell transformation. HBV has a synergistic effect with aflatoxines during the development of an HCC. These aflatoxines are difurane-coumarin derivatives which often accumulate in spoilt foods as a metabolic product of the mould fungus *Aspergillus flavus*. This poison has a highly mutagenic potential and can interact with the tumor suppressor p53. In patients who were exposed to a high aflatoxin concentration, mutations in the p53 gene were found more often. Furthermore, co-infections with HBV and HCV also lead to a higher risk of developing HCC.

For the prevention of a HBV infection, various ways have been tried within the past two decades. Thus, the number of infections in the Western industrial nations has been reduced to a minimum by extensive vaccination programmes. In rare cases, however, acute hepatitis B infection followed by chronically persistent hepatitis B infection can occur despite vaccination. If the first symptoms of an acute HBV infection are recognised, a late vaccination or passive immunisation with α-HBV immunoglobulins can prevent a spreading.

With chronically infected patients, administration of interferon α can eliminate the virus from the liver in 20-30% of the cases and clearly reduce the number of viruses in the blood in another 30%. In recent times, a number of nucleoside analogues have been discovered which inhibit the reverse transcriptase of HBV. Lamivudin has already been introduced into clinical application. Further nucleoside analogues such as for example Famciclovir are being tested clinically. Disadvantages of the antiviral therapy are the fact that the disease often recurs as soon as the pharmaceutical agent is no longer administered. Also, resistant variants specific to the nucleoside analogues form relatively quickly. Thus, this treatment method for a long-term treatment seems doubtful and, with regard to the evolutionary selection of HBV, in favour of resistant HBV strains, questionable from an epidermiologic point of view.

Thus, there is a great need to, both, treat existing infections caused by hepatitis B virus, particularly by strains resistant to nucleoside analogues, and to counteract in a prophylactic way the onset in high-risk groups such as e.g. drug addicts or children of infected mothers. Therefore, the problem underlying the present invention is to provide means and ways to treat infections caused by hepatitis B viruses resistant to nucleoside analogues and diseases based thereon and to prevent their onset by prophylaxis. This task has been solved by the embodiments characterised in the claims.

Thus, the invention relates to the use of one or more *Phyllanthus* component(s) or substances or mixtures of substances obtained therefrom for the prevention or treatment of infectious diseases caused by a hepatitis B virus which is resistant to nucleoside analogues or in the development or progression of which a hepatitis B virus resistant to nucleoside analogues plays a role.

According to the invention, the term "*Phyllanthus* component(s)" relates to all the constituents of the whole plants such as e.g. leaves, bark, blossoms, seeds, fruits, stalks, branches, stems, roots and wood, as well as parts thereof such as e.g. leaf or roots apexes. These *Phyllanthus* constituents can exhibit the same, similar or non-related ingredients. Therefore, different *Phyllanthus* constituents can be used individually or together and different *Phyllanthus* constituents of different *Phyllanthus* species can be used individually or together. "Several" *Phyllanthus* constituents relates to the all the *Phyllanthus* constituents, for example, in form of whole plants or extracts thereof. The *Phyllanthus* constituents can be. used after pre-treatment or without pre-treatment. Pre-treatment could, for example, comprise procedures such as the drying of leaves.

"Substances or mixtures of substances" which can be obtained from *Phyllanthus* constituents mainly relate to active agents. These can be used in pure or impure form. These active agents can be used individually or in combination as active agents or mixture of active agents. In this context, different active agents can be present in different *Phyllanthus* constituents or in the same *Phyllanthus* constituents. Mixtures of active agents can be obtained from the same *Phyllanthus* component or from different *Phyllanthus* constituents. In this context, obtaining of the active agents from the different *Phyllanthus* constituents can take place individually, to start with, wherein, subsequently, the individual active agents are united to form a mixture of active agents, or, at the same time, a mixture of active agents can be obtained from *Phyllanthus* constituents united earlier. Substances or mixtures of substances according to the invention can consist of the same or of different representatives of a class of chemical compounds. These chemical compounds can be used in natural form, i.e. unmodified by the obtaining process or modified by the obtaining process. The chemical compounds can, for example, be cyclic or branched or non-branched polar or non-polar hydrocarbons, lipids, lipid derivatives, nucleic acids, nucleotides, nucleotide derivatives, nucleosides, nucleoside derivatives, polypeptides, peptides, amino acids or modified amino acids. In this context, derivatives relate to all the compounds that can be derived from the compounds mentioned and can be achieved by chemical modification. For example, such derivatives can be formed by substitution, addition, esterification, saponification or condensation reactions.

Within the meaning of the present invention, "prevention" relates to the use of *Phyllanthus* constituents or substances or mixtures of substances obtained therefrom as a phrophylaxis for the prevention of the infection with hepatitis B virus resistant to nucleoside analogues or for the reduction of the virus load. Furthermore, according to the invention, this relates to avoiding the breakout of the disease or achieving a less severe breakout of the disease. The *Phyllanthus* constituents or substances or mixtures of substances used for prevention can be different from or identical to the *Phyllanthus* constituents or substances or mixtures of substances used for treatment. The use for prevention can take place in a different or the same dose and by a different or the same application as in the use for treatment. Prevention can take place by a one-off or by several application(s). The dose of *Phyllanthus* constituents or substances or mixtures of substances used for prevention should, however, essentially offer sufficient protection against infectious diseases caused by hepatitis B viruses which are resistant to nucleoside analogues or in the development or progression of which these viruses play a role. At the same time, the dose used for prevention should not have a harming effect on the organism.

During the use of one or more *Phyllanthus* constituents or substances or mixtures of substances obtained therefrom according to the invention for the treatment of infectious diseases, these *Phyllanthus* constituents or substances or mixtures of substances obtained therefrom can be used in a similar way as described for the prevention. The dose used for the treatment can fight both the cause of the infectious diseases, i.e. the viruses and their growth in the organism, and the symptoms of the infectious diseases. In general, it has to be stated that the use of natural therapeutics, such as *Phyllanthus* constituents or substances or mixtures of substances obtained therefrom is advantageous both for the prevention and the treatment of infectious diseases due to nucleoside analogue resistant HBV and, secondary, diseases caused thereby, since with natural therapeutics, fewer side effects having an additional straining effect on the organism are to be expected due to an improved pharmaceutical acceptability.

For the treatment, the constituents and substances or mixtures of substances are formulated as pharmaceutical compositions, medicinal products or medicinal adjuvant. For the definition of pharmaceutical compositions see the description below.

Infectious diseases are in particular characterised by an immune response being triggered in the organism, caused by a pathogen. The objective of this immune response is to fight the pathogen. Thereby, however, severe damage to the cells and the tissues of the organism concerned can be caused which, in this case, can be caused by the immune system itself. In addition, in the case of infectious diseases, the pathogen itself may cause damage, since, for example in infected cells, metabolic processes or differentiation programmes can be deleted which have a damaging effect on the organism. Cause and symptoms of the infectious diseases can relate to identical cells or tissue but also different ones. Thus, for example, a modified liver metabolism could lead to a modification of the composition of the proteins contained in the blood, in particular the enzymes, which could, again, lead to damage of other organs, e.g. the kidney. Thus, the use of *Phyllanthus* component(s) or substances or mixtures of substances obtained therefrom according to the invention not only relates to the prevention or treatment of causes of infectious diseases, such as e.g. an infection by viruses, but also the prevention or treatment of symptoms occurring secondarily which are due to the presence of the pathogen in the organism.

Within the meaning of the invention, "pathogen" relates to a hepatitis B virus which is resistant to nucleoside analogues. Within the meaning of the invention, the hepatitis B virus in total comprises eight different subtypes characterised in that they all cause threatening diseases. In this context, hepatitis is of particular importance; it leads to modifications of the morphology and, at the same time, of the function of the liver, which are life-threatening for the organism. Furthermore, due to the ways of transmission for these viruses, in particular saliva and blood, prophylactic measures such as the use of *Phyllanthus* constituents or substances or mixtures of substances obtained therefrom according to the invention are shown for the prevention. The *Phyllanthus* constituents or substances or mixtures of substances obtained therefrom according to the invention can alleviate the infectious disease caused by hepatitis B viruses which are resistant to nucleoside analogues, in particular by inhibition of the growth of the viruses in the cells and tissues affected. This can take place, for example, by the inhibition of individual or different enzymes underlying the cellular changes in connection with the infectious disease. The *Phyllanthus* constituents or substances or mixtures of substances obtained therefrom used according to the invention, however, can, additionally for example as immune modulators, positively influence a prevention or treatment of infectious diseases caused by viruses of the family of the Flaviviridae.

The term "development or progression" relates to the fact that the hepatitis B viruses which are resistant to nucleoside analogues can as pathogens either be the cause and, therefore, play a part either alone or in combination with other pathogens or, however, can promote the progression of an existing infectious disease either alone or in combination with other pathogens.

The use according to the invention shows surprising and unexpected positive effects during the prevention or treatment of infectious diseases which are due to infections by hepatitis B viruses which are resistant to nucleoside analogues.

From the data known so far about the effects of known therapeutics, particularly nucleoside analogues, these positive and surprising effects were not to be expected. Due to the development of resistances of various hepatitis B virus stems against the pharmaceutical compositions already used for treatment, including nucleoside analogues, such as e.g. Lamivudine and Famciclovir, a successful treatment by *Phyllanthus* constituents or substances or mixtures of substances obtained therefrom was not to be expected. Even if, as a starting point, one takes the positive pharmaceutical effects against the hepatitis B virus by application of *Phyllanthus* constituents which is known in the state of the art, it is by no means obvious that, with regard to the lack of therapeutic effects on mutated hepatitis B virus stems for which resistances against other active agents could be shown already, the pharmaceutical effect of *Phyllanthus* constituents differs from said other active agents. Considering these facts, the data obtained in vitro to start with regard to the inhibition of the gene expression and the virus replication of hepatitis B viruses which are resistant to Lamivudine, in particular the so-called "YMDD hepatitis B virus", are all the more surprising.

Furthermore, the invention relates to the use of one or more *Phyllanthus* component(s) or substances or mixture of substances obtained therefrom for the production of a pharmaceutical composition for the prevention or treatment of infectious diseases caused by a hepatitis B virus which is resistant to nucleoside analogues or in the development or progression of which the hepatitis B virus resistant to nucleoside analogues plays a role.

According to the invention, pharmaceutical compositions are substances and preparations of substances which are meant to alleviate, prevent or recognise diseases, ailments, damage to the body or disease-related discomforts by means of application on or in the human body.

According to the invention, medicinal products are substances or preparations of substances used alone or in combination with each other or other subjects meant by the manufacturer to serve for the application for humans by means of their functions with the purpose of recognising, preventing, monitoring, treating or alleviating diseases and whose main effect in or on the human body, according to its objective, is achieved neither by agents with a pharmacological or immunological effect nor by metabolisms whose effectiveness, however, can be supported by such agents.

According to the invention, medicinal adjuvants are substances which are used for the production (as active ingredients) of pharmaceutical compositions.

The essential terms of this embodiment have been explained and defined above. The formulation of the pharmaceutical composition containing the *Phyllanthus* constituents or substances or mixtures of substances obtained therefrom optionally takes place in combination with a pharmaceutically acceptable carrier and/or diluent.

Examples of suitable pharmaceutically acceptable carriers are known to the person skilled in the art and comprise phosphate-buffered sodium chloride solutions, water, emulsions such as e.g. oil/water emulsions, various types of detergents, sterile solutions, and so on. Pharmaceutical compositions comprising such carriers can be formulated by means of conventional methods known. These pharmaceutical compositions can be administered to an individual in an appropriate dose, e.g. in a range of 1 µg to 100 mg per day and patient. The administration can take place in various ways, e.g. in an intravenous, intraperitoneal, a subcutane, intramuscular, local or intradermal way. The type of dosage is determined by the doctor in charge according to the clinical factors. It is known to the person skilled in the art that the type of dosage depends on various factors such as e.g. the size, the body surface, the age, the sex or the general health of a patient, but also on the specific preparation which is administered, the duration and kind of application and on other drugs possibly being administered at the same time.

In a preferred embodiment of the invention, the infectious disease is yellow fever, cirrhosis or hepatocellular carcinoma.

With regard to the characteristic symptoms of the diseases mentioned, we refer to standard text books of medicine such as e.g. Pschyrembel "Klinisches Wörterbuch", Walter de Gruyter, Berlin (1994, 2000).

Furthermore, the invention relates to the use of one or more *Phyllanthus* component(s) or substances or mixtures of substances obtained therefrom for the inhibition of amplification of the hepatitis B virus which is resistant to nucleoside analogues.

"Inhibition of amplification of hepatitis B viruses which are resistant to nucleoside analogues" relates to the fact that the replication of the viruses in the affected host cell or virus budding from an infected host cell or both is prevented. Moreover, the infection of further host cells of the viruses could be prevented and amplification of the viruses could be achieved by means of blocking of the target cells (host cells). During the inhibition of the formation of new viruses in an infected host cell, enzymes which play a role in the formation of new viruses, above all, can be inhibited. In particular, these are enzymes which play a role, for example, in the replication of the viral nucleic acids (reverse transcriptases, polymerases and helicases) or in the processing of viral proteins (proteases). The inhibition of amplification by inhibition of virus budding from an infected host cell could be caused, in particular, by the inhibition of the viral and/or cellular proteins essential for the budding process. The inhibition of amplification of the blockage of further host cells could be achieved by inhibition of the mechanisms which play a role in the recognition of host cells and viruses or which play a role in the uptake of the virus into the host cell or by inhibition.

In a preferred embodiment, the inhibition takes place ex vivo or in vitro.

This embodiment is of interest, in particular, for the further development of active agents according to the invention, the analysis of new active agents or for the quality control thereof. In particular, the inhibition can be carried out outside the organism, too, in isolated cells or tissues, e.g. in cell culture. In particular, in in vitro systems, e.g. in cell cultures, it can be analysed which constituents of *Phyllanthus* exhibits the most advantageous characteristics. Thus, an optimising of the substances or mixtures of substances can be carried out on the basis of in vitro test systems. Preferably, for this purpose, *Phyllanthus* constituents are divided into groups of active agents or in single constituents according to common chemical/physical methods and the single constituents in such test systems are tested for inhibition of virus growth.

In another preferred embodiment of the invention, the one or more *Phyllanthus* component(s) or substances or mixtures of substances obtained therefrom are derived from *Phyllanthus amarus, Phyllanthus niruri, Phyllanthus emblica, Phyllanthus urinaria, Phyllanthus acidus, Phyllanthus acuminatus* and *Phyllanthus reticulatus* or from several of these *Phyllanthus* species.

In another preferred embodiment of the invention, the hepatitis B virus which is resistant to nucleoside analogues exhibits one or more mutations in the reverse transcriptase.

According to the invention, the term "one or more mutations" means one or more mutations in the nucleic acid sequences of the virus or in the amino acid sequences of polypeptides derived therefrom. Here, nucleic acids can comprise particularly DNA or RNA. The mutations present in the nucleic acid sequence can lead to the substitution of an amino acid in the amino acid sequence of the viral polypeptides, which can be responsible for the change of the function of viral polypeptides. In this context, the function of enzymes of the virus can in particular be influenced. The enzymes created in this connection can be responsible for the resistances of hepatitis B virus strains formed against common active agents as e.g. Lamivudine or Famciclovir. Moreover, mutations at the nucleic acid level can, of course, also interfere with the efficiency of the transcription and/or the efficiency of the translation of various parts of the viral genome and can thus influence the intracellular concentration of the viral enzymes in the affected host cell in a positive or negative way.

"Reverse transcriptase" means an enzyme with the property of a DNA or RNA dependent DNA polymerase. Both retroviruses and hepatitis viruses have such a reverse transcriptase. In the case of the hepatitis B virus, the reverse transcriptase encoded by the viral genome is a multifunctional enzyme. The reverse transcriptase can be divided into four domains, on the one hand, the functional domains of the polymerase and RNase H activity and, on the other hand, the structural domains. The reactions catalysed by the reverse transcriptase occur analogously to the normal DNA polymerase reactions, and as is the case with the other DNA polymerases, a primer is also necessary here. At first, the RNA template is normally a single strand and a single complementary DNA strand is synthesised so that an RNA-DNA hybrid is formed. Often, a short polydeoxyribothymidine acid—poly(dT)—is a suitable primer as it attaches to the polyriboadenylic acid tail which eucaryotic mRNAs normally have. Thus, the synthesis of a DNA copy (of a cDNA) of the RNA is achieved.

The cDNA copy of the mRNA can be transferred into a double stranded DNA if the original RNA template is removed with RNaseH or by alkaline hydrolysis. The single stranded DNA product serves as its own primer (and as template) for the synthesis of the complementary second DNA strand. This reaction can be catalysed either by the DNA polymerase I or by the reverse transcriptase itself. Apparently, a short hairpin loop is formed near the 3'-hydroxyl end of the first strand which means that a primer is available. The complete double strand still carries at one end the hairpin loop, which is eventually split off by a single-strand specific nuclease, so that two completely complementary DNA single strands (a cDNA double strand) are formed.

In a particularly preferred embodiment of the invention, the one or more mutations comprise a substitution of an isoleucine by a methionine at the position 552 or at a corresponding position.

The substitution of an isoleucine by a methionine at position 552 of the viral reverse transcriptase is characteristic for the YMDD hepatitis B virus mutant which was already described and is resistant to Lamivudine. This substitution apparently leads to a resistance of the YMDD hepatitis B virus strain against Lamivudine and other nucleoside analogues in cell culture.

According the invention a "corresponding position" to position 552 is to be understood as a substitution of an isoleucine by a methionine in the amino acid motif YMDD, wherein the YMDD amino acid motif does not necessarily have to be at positions 551 to 554, but e.g. it can be moved by possible deletions or additions of nucleotides on the nucleic acid level.

In another preferred embodiment of the invention the prevention or treatment comprises the inhibition of one or more viral enzymes.

The inhibition of one or more vial enzymes means that the function of these enzymes is either directly or indirectly influenced in a negative way. A direct inhibition can e.g. (the inventors not wanting to be bound to a scientific therapy here or in the other embodiments) be the case by interaction of one or more inhibitory substances contained in the *Phyllanthus* constituents or in substances or in mixtures of substances obtained therefrom according to the invention with one or more enzymes or an indirect inhibition by interaction of these inhibitors with factors which are either necessary for the expression, the translation or the processing of these enzymes. Particularly this is to be understood as the inhibition of viral enzymes as e.g. helicases, polymerases, reverse transcriptases or proteases. A direct inhibition of these enzymes could e.g. be based on the interaction of inhibitors which are contained in *Phyllanthus* constituents or in substances or mixtures of substance obtained therefrom with the catalytic centre of these enzymes or with a domain which regulates the activity. Moreover, cellular enzymes, too, which e.g. contribute to the expression, translation or post-translational modification of the viral enzymes and thus direct their function could be either impaired or additionally impaired by these inhibitors. In any case, however, by the inhibition of one or more viral enzymes according to the invention the proliferation and/or the infectious disease resulting from the attack by the virus or its development or progression is alleviated.

In a particularly preferred embodiment of the invention, the inhibition comprises the inhibition of the processing of one or more viral enzymes.

Among the previously described post-translational modification of viral enzymes by *Phyllanthus* constituents or substances or mixture of substances obtained therefrom according to the invention, the processing of one of more viral enzymes is most important. Processing means that at an enzyme which is at first inactive is activated by post-translational modifications, e.g. proteolytic cleavage, phosphorylation or glycosylation. Thus, by the inhibition of the processing of one or more viral enzymes according to the invention the function of these enzymes can be limited or completely inhibited. The *Phyllanthus* constituents or the substances or mixture of substances obtained therefrom according to the invention which are used for the inhibition of the processing can, in this context, inhibit either one or more viral enzymes at the same time. This can be carried out either by inhibition of the same or by inhibition of different processing steps which are necessary for the activation of the enzyme.

In a further particularly preferred embodiment, an enzyme is the reverse transcriptase.

The term "reverse transcriptase" is to be understood in accordance with the definition given above.

In another particularly preferred embodiment, the reverse transcriptase has a substitution of an isoleucine by a methionine at position 552 or at a corresponding position.

The meaning of the substitution of the isoleucine by a methionine at position 552 has already been referred to above.

In an embodiment of the invention which is also preferred, the nucleoside analogues are selected from the group consisting of Lamivudine and Famciclovir.

In a further preferred embodiment of the invention, the *Phyllanthus* constituents comprise the herb drug, the leaves, the bark, the blossoms, the seed, the fruits, the stalks, the branches, the stem, the root and the wood.

In another preferred embodiment, the substances or mixtures of substances are selected from the group consisting of alkaloids, tanning agents, lignans, sesquiterpenes, triterpenes and cyanogenic glycosides.

Alkaloids are a group of substances which is outstanding in that it contains one or more nitrogen atoms, mostly has a heterocycle and is in general bound to a plant acid in a salt-like manner. From a chemical point of view, protoalkaloids, among these are also biogenic amines as precursors of alkaloids, and pseudoalkaloids can be distinguished. Derivatives of certain acid families as e.g. precursors can be understood by alkaloids in a narrower sense. Another important class of substances among the substances or mixtures of substances which can be recovered are the so-called cyanogenic glycosides. Glycosides comprise constituents which are created, with an efflux of water, by the reaction of the acetalic hydroxy group at the C1 atom of a sugar with OH groups of alcohols and phenols or other sugars, NH-groups of amines or SH groups of isothiocyanate. Typical representatives of cyanogenic glycosides are taxiphyllin and 2-hydroxy-2-(4-hydroxyphenyl)acetonitrile. Tanning agents are particularly characterised by phenolic hydroxy groups. The group of terpenes which comprises the sesquiterpenes and the triterpenes consists of unsaturated hydrocarbons which consists of basic isoprene units and are present as polymers. The substances and mixtures of substances of the invention can be present as pure substance or they can have contaminations. Moreover, mixtures of substances can consist of different members of this group and, furthermore, they can contain other additional substances or mixtures of substances.

In a particularly preferred embodiment of the use according to the invention, aqueous non-polar, branched or linear chain hydrocarbons are used together with n-hexane for the extraction of the substance of the mixture of substances.

Non-polar, branched or linear chain hydrocarbons particularly serve as solvent during the extraction of substances or mixtures of substances from *Phyllanthus* constituents, wherein the non-polar solvent are in particular characterised in that they do not contain polar groups. Among these are e.g. benzole or saturated hydrocarbons. The hydrocarbons of the invention should in particular be characterised by a framework of hydrocarbon atoms of 5 to 10 atoms (C5- to C10-framework). Extraction means to selectively solubilize substances or mixtures of substances in order to recover them. The behaviour upon solvation is influenced by the solvent used.

In a particularly preferred embodiment, aqueous, non-polar, branched or linear chain hydrocarbons are used together with n-hexane for the extraction of the substance or the mixture of substances.

In a further particularly preferred embodiment, the hydrocarbons have a C5 to C10 framework.

In another particularly preferred embodiment, alcohols and/or a mixture thereof is used for the extraction of the substance or the mixture of substances.

In particular, alcohols are hydrocarbons having one or more OH-groups at hydrocarbon atoms. For the extraction of the substances or mixtures of substances of the invention, particularly alcohols with a framework of 1 to 4 hydrocarbon atoms and/or mixtures thereof are used. Here, methanol or ethanol mixtures thereof are of particular importance.

In another particularly preferred embodiment, the alcohols used are short chain primary C1 to C4 alcohols and/or mixtures thereof.

In another particularly preferred embodiment of the invention, the alcohols used are methanol and/or ethanol.

In a preferred embodiment, one or more *Phyllanthus* constituents or the substances or mixture of substances obtained therefrom are used in combination with other active agents.

The *Phyllanthus* constituents or the substances or mixtures of substances obtained therefrom according to the invention can also be used in combination, i.e. either directly as a mixture, in parallel or subsequently together with other active agents. The other active agents, are above, all the pharmaceutical compositions which are known in the therapy of infectious diseases caused by a hepatitis B virus which is resistant to nucleoside analogues.

In a particularly preferred embodiment, the other active agents are selected from the group consisting of interferon α, interferon β, interferon γ and ribavirin.

Active agents in the treatment or prevention of infectious diseases which are based on members of the Flaviviridae family, interferon α, interferon β, interferon γ and ribavirin have shown especially effective. In this context, the effect of interferons is based above all on their modulating effect on the cells of the immune system. A combination therapy with two or more of these active agents should prove especially favourable for the prevention and for the treatment of the course of disease.

In a particularly preferred embodiment of the invention, the application is made in the form of an infusion solution, injection solution, a tablet, an ointment, a healing pack, a granular powder, a food additive or in the form of clysters.

*Phyllanthus* constituents or substances or mixtures of substances obtained therefrom can be used in various forms either separately or in combination. In particular, the *Phyllanthus* constituents or the substances or mixtures of substances obtained therefrom can be applied in the form of infusion solutions or injection solutions. Here, a pharmaceutically acceptable solvent is added to the active agents isolated from *Phyllanthus* constituents or substances or mixtures of substances obtained therefrom in pure or impure form and are introduced into the bloodstream of a patient suffering from an infectious disease which is caused by the infection by hepatitis B viruses which are resistant to nucleoside analogues. Thus, infusion solutions and injection solutions are a particular suitable form of application for the treatment. Tablets are a mixture of active agents or adjuvants in the form of a powder or granular powder the shapes of which are regular and always the same (e.g. the shape of a disk, cylinder, oval-, spherical-, rod- or dice-shaped) for a uniform dosage. In this context, the active agents can be isolated in pure or impure form from the *Phyllanthus* constituents of substances or mixtures of substances obtained therefrom according to the invention. Here, the adjuvants are particularly used in connection with the pharmaceutical acceptability and they are used for the preservation and storability of the active agents. An ointment with an active agent which can be present in pure or impure form and which can be produced from the *Phyllanthus* constituents or the substances or mixtures of substances obtained therefrom according to the invention is a pharmaceutical preparation the form of which can be plastically changed, which comprises the active agent and an ointment base as basis or vehicle. Healing packs, in particular, comprise either the *Phyllanthus* constituents of the invention as such or the substances or mixtures of substances obtained therefrom in pure or impure form and the active agents isolated from the *Phyllanthus* constituents or the substances or mixtures of substances in pure and impure form in combination with support materials and further active agents. A granular powder is a coarse-grained, graniferous powder mixture containing active agents from the *Phyllanthus* constituents or the substances or mixtures of substances obtained therefrom according to the invention. A granular powder can also have the form of tablets. The *Phyllanthus* constituents or the substances or mixtures of substances obtained therefrom according to the invention can also be used as food additives. These are the use of *Phyllanthus* constituents in the form of foodstuffs and in particular also food additives e.g. in the form of tablets, granular powders or curative teas.

In another preferred embodiment of the invention, the application is carried out in an oral, a topical or a parenteral way.

The invention moreover refers to methods for the prevention or treatment of infectious diseases in a mammal which is caused by a hepatitis B virus which is resistant to nucleoside analogues or at the development or progression of which a hepatitis B virus which is resistant to nucleoside analogues participates, wherein one or more *Phyllanthus* component(s) or substances or mixtures of substances are administered to the mammal.

The method according to the invention can, together with the step of administering one or more *Phyllanthus* constituents or substances or mixtures of substances obtained therefrom, also comprise other steps, e.g. the administration of other therapeutics or additional therapeutic measures. For the methods according to the invention or the terms which are used for describing them, the definitions according to the applications of the invention also apply. Moreover, the methods of the invention also comprise all embodiments of the application of the invention.

In a preferred embodiment of the invention, the mammal is a human.

Moreover, the invention refers to a method for inhibiting the amplification of a hepatitis B virus which is resistant to nucleoside analogues, wherein one or more *Phyllanthus* component(s) or substances or mixtures of substances obtained therefrom are contacted with the viruses.

In a preferred embodiment, the inhibition is carried out ex vivo or in vitro.

In a particularly preferred embodiment of the invention the nucleoside analogues are selected from a group consisting of Lamivudine and Famciclovir.

The other preferred or particularly preferred embodiments described for the application of the invention apply mutatis mutandis also for the methods of the invention.

The figure shows:

FIG. 1 (*b*) shows the dose-dependent inhibition of the "YMDD (isoleucin) mutant"-HBV-DNA formation in HuH7 cells. The *Phyllanthus amarus* extract was tested in concentrations of 0 (negative control) to 1,000 µg/ml. Lane 1 shows the negative control (no virus was transfected). Lane 2 shows the new synthesis of DNA (virus descendants) in the absence of the *Phyllanthus amarus* extract. Lane 3 shows a positive control (compared to lane 2 half of the HBV DNA was transfected). Lane 4 shows the molecular weight standard (1 kb ladder). Lanes 5 to 8 show the new formation of HBV DNA (virus descendants) in the presence of 100 (lane 5), 200 (lane 6), 500 (lane 7) and 1,000 (lane 8) µg/ml *Phyllanthus amarus*.

The examples explain the invention.

EXAMPLE 1

Figure 1:
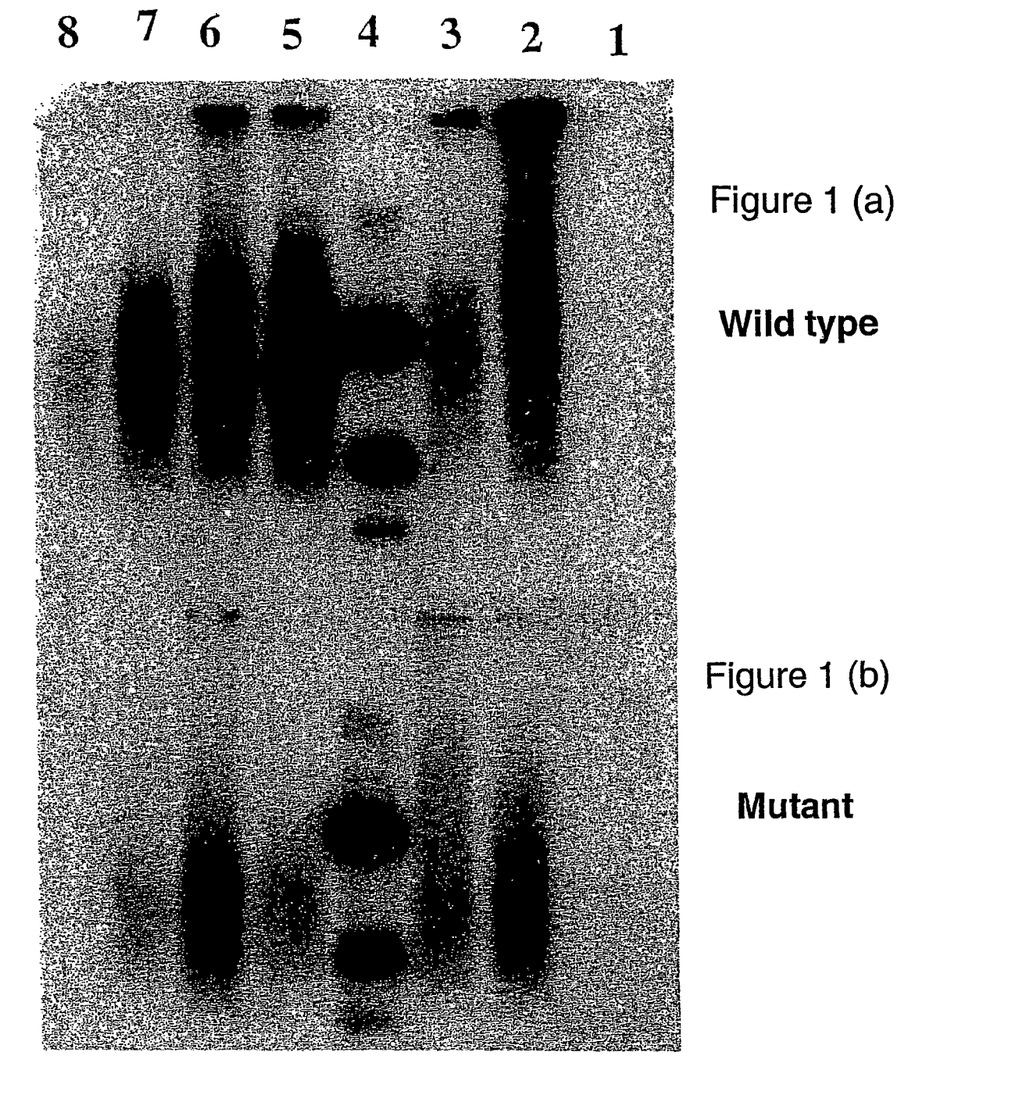
FIG. 1: In HuH7-cells *Phyllanthus amarus* extract inhibits the "de novo" synthesis of viral DNA in a dose-dependent manner FIG. 1(*a*) shows the dose-dependent inhibition of "wild type" HBV-DNA in HuH7 cells. The *Phyllanthus amarus* extract was tested with concentrations of 0 (negative control) to 1,000 µg/ml. Lane 1 shows the negative control (no virus was transfected). Lane 2 shows the new synthesis of DNA (virus descendants) in the absence of *Phyllanthus amarus* extract. Lane 3 shows a positive control (compared to lane 2 half of the HBV-DNA was transfected). Lane 4 shows the molecular weight standard (1 kb ladder). Lanes 5 to 8 show the new formation of HBV-DNA (virus descendants) in the presence of 100 (lane 5), 250 (lane 6), 500 (lane 7) and 1,000 (lane 8) µg/ml *Phyllanthus amarus*.

In Vitro Inhibition of the Gene Expression and the Replication of Lamivudine Resistant (YMDD) Hepatitis B Viruses The inhibitory effect of *Phyllanthus amarus* constituents or of substances obtained therefrom on the gene expression and the replication of "wild type" and Lamivudine-resistant (YMDD) hepatitis B viruses was tested in a cell culture model, cf. also FIG. 1. In these experiments, a standardised extract with LAT No. 01620514 on an aqueous basis which was provided by Prof. Wagner, Munich, was used. HuH7 cells were at first cultivated in 5% $CO_2$ at 37° C. in Dulbecco's modified Eagle Medium to which 10% fetal calf serum, glutamine and penicillin streptomycin had been added. A *mycoplasma* contamination of the cell culture was excluded by corresponding tests. The cytotoxicity of the *Phyllanthus amarus* extract was at first tested in WST1 Assay (Boehringer Mannheim). A cytotoxicity of the extract could thus be excluded. Subsequently, about $10^6$ HuH7 cells were plated and cultivated over night. On the next day, these cells were transfected with 15 µg of the plasmid DNA PHBV1.5 or a plasmid containing the genome of the Lamivudine-resistant YMDD hepatitis B virus mutant by the calcium phosphate method. The transfection efficiency was controlled by co-transfection of 1 µg of a β-galactosidase expression plasmid by detection of the β-galactosidase activity. The transfected HuH7 cells were cultivated for 5 days in a medium containing 100, 250, 500 or 1,000 µg/ml of the *Phyllanthus amarus* extract. Subsequently, the cells were washed in PBS, collected and homogenised. The homogenised cell suspension was centrifuged in a micro centrifuge at maximum speed. The supernatants were collected and incubated with protein A agarose beads loaded with anti HBC antibodies. After incubation, the beads were washed three times with TNE buffer and were incubated therein for 12 hours at 4° C. After the last washing step, the pelleted beads were incubated with DNase (1 U/ml) and RNase (1 U/µl) in TNE buffer in the presence of magnesium chloride for 30 minutes at 37° C. After washing the pellet three times with TNE buffer, a treatment with proteinase K (0.5 mg/ml) in the presence of sodium dodecylsulfate (1%) and Sacrosyl for 12 hours at 37° C. so as to release the viral DNA contained in the hepatitis B particles purified by the beads. Subsequently, the DNA was extracted with phenolchlorophorm isoamyl alcohol (25:24:1) and was precipitated in the presence of 10 µg tRNA. The DNA pellet was then resuspended in 20 µl TE buffer and was cleaved in a 1% alkaline agarose gel under denaturating conditions. Subsequently, a Southern analysis was carried out wherein the DNA was transferred onto a nylon membrane (Qiabrane Nylon, Qiagen, Germany). In order to detect the viral DNA monomeric DNA was isolated from the plasmid pHBV1.5 and was labelled by a random priming procedure with a radionuclide $^{32}P$. In a subsequent hybridisation, $10^6$ cpm/ml of this labelled probe were used. The data obtained show that the *Phyllanthus amarus* extract significantly inhibits the "de novo" synthesis of viral DNA dependent on the dose of the extract used. The inhibition of the de novo synthesis of viral DNA could be observed in "wild type" hepatitis B viruses already at a concentration of 250 µg/ml *Phyllanthus amarus* extract, in the case of Lamivudine-resistant YMDD hepatitis B virus mutants at a concentration of from 500 to 1,000 mg/ml. The observed effects are in no case caused by the cytotoxicity of the *Phyllanthus amarus* extract.

The invention claimed is:

1. A method of inhibiting synthesis of viral DNA in a mammal infected with a YMDD hepatitis B virus mutant strain resistant to lamivudine comprising administering an effective amount of at least one an aqueous or alcohol extract of *Phyllanthus* to a mammal infected with the YMDD hepatitis B virus mutant strain resistant; and, inhibiting YMDD hepatitis B virus mutant strain viral DNA synthesis in the mammal using the aqueous or alcohol extract of *Phyllanthus*.

2. The method according to claim 1, wherein the *Phyllanthus* is selected from the group consisting of: *Phyllanthus amarus, Phyllanthus niruri, Phyllanthus embilica, Phyllanthus urinaria, Phyllanthus acidus, Phyllanthus acuminatus*, and *Phyllanthus reticulatus*.

3. The method according to claim 1, wherein the mammal is a human.

4. The method according to claim 1, wherein administering comprises contacting the YMDD hepatitis B virus mutant strain with the aqueous or alcohol extract of *Phyllanthus*.

5. The method according to claim 1, further comprising inhibiting amplification of the YMDD hepatitis B virus mutant strain in the mammal using the aqueous or alcohol extract of *Phyllanthus*.

6. The method according to claim 1, further comprising inhibiting at least one viral enzyme using the aqeuous or alcohol extract of *Phyllanthus*.

7. The method according to claim 6, further comprising inhibiting at least one viral reverse transcriptase.

8. The method according to claim 1, wherein the aqueous or alcohol extract of *Phyllanthus* component or substance is derived from at least one of the group consisting of *Phyllanthus* leaf, bark, blossom, fruit, seed, stalk, branch, stem, root, wood, and any combinations thereof.

9. The method according to claim 1, wherein the aqueous or alcohol extract of *Phyllanthus* comprises at least one component or substance selected from the group consisting of alkaloids, tanning agents, lignanes, sesquiterpenes, triterpenes, cyanogenic glycosides, and any combinations thereof.

10. The method according to claim 1, wherein the extract is extracted from *Phyllanthus* using an alcohol or alcohol mixture.

11. The method according to claim 10 wherein the alcohol comprises at least one short-chain primary C1 to C4-alcohols and/or mixtures thereof.

12. The method according to claim 1, further comprising administering an additional active agent substantially concurrently with the aqueous or alcohol extract of *Phyllanthus* component or substance.

13. The method according to claim 12, wherein the active agent comprises an interferon or ribavirin.

14. The method according to claim 12, wherein the active agent comprises an interferon selected from the group consisting of interferon $\alpha$, interferon $\beta$, interferon $\gamma$, and any combinations thereof.

15. The method according to claim 1, wherein the administering comprises administering the aqueous or alcohol extract of *Phyllanthus* orally, topically or parenterally.

16. The method according to claim 1, wherein the YMDD hepatitis B virus mutant strain comprises a substitution of an isoleucine by a methionine in a YMDD amino acid motif of a viral reverse transcriptase.

17. The method according to claim 16, wherein the substitution of an isoleucine by a methionine in a YMDD amino acid motif of the viral reverse transcriptase is at position 552.

\* \* \* \* \*